United States Patent [19]

Buckley, III

[11] Patent Number: 4,933,485

[45] Date of Patent: Jun. 12, 1990

[54] LUBRICATING OIL COMPOSITIONS CONTAINING VERY LONG CHAIN ALKYLPHENYL POLY (OXYALKYLENE) AMINOCARBAMATES

[75] Inventor: Thomas F. Buckley, III, Hercules, Calif.

[73] Assignee: Chevron Research Company, San Francisco, Calif.

[21] Appl. No.: 112,902

[22] Filed: Oct. 23, 1987

[51] Int. Cl.$^5$ ............... C07C 125/04; C10M 133/00; C10L 1/22

[52] U.S. Cl. .................... 560/159; 560/158; 44/63; 44/71; 252/51.5 R

[58] Field of Search ............ 252/51.5 R, 51.5 A; 44/63, 71; 560/158, 159

[56] References Cited

U.S. PATENT DOCUMENTS

| | | | |
|---|---|---|---|
| 2,991,162 | 7/1961 | Malec | 44/58 |
| 4,160,648 | 7/1979 | Lewis et al. | 44/63 |
| 4,191,537 | 3/1980 | Lewis et al. | 44/71 |
| 4,197,409 | 4/1980 | Lilburn | 560/158 |
| 4,198,306 | 4/1980 | Lewis | 252/51.5 R |
| 4,233,168 | 11/1980 | Lewis | 252/51.5 A |
| 4,236,020 | 11/1980 | Lewis | 560/159 |
| 4,243,798 | 1/1981 | Franklin et al. | 528/371 |
| 4,270,930 | 6/1981 | Campbell et al. | 44/71 |
| 4,274,837 | 6/1981 | Lilburn | 44/63 |
| 4,275,006 | 6/1981 | Erdman | 252/47.5 X |
| 4,288,612 | 9/1981 | Lewis | 560/159 |
| 4,289,634 | 9/1981 | Lewis | 252/32.5 |
| 4,294,714 | 10/1981 | Lewis | 252/34 |
| 4,329,240 | 5/1982 | Lilburn | 252/51.5 A |
| 4,410,437 | 10/1983 | Erdman | 252/47.5 |
| 4,438,022 | 3/1984 | Campbell | 252/51.5 R |
| 4,521,610 | 6/1985 | Plavac | 560/27 |
| 4,537,693 | 8/1985 | Campbell | 252/51.5 R |
| 4,568,358 | 2/1986 | Courtney | 44/57 |
| 4,604,103 | 8/1986 | Campbell | 44/72 |
| 4,695,291 | 9/1987 | Plavac | 44/62 |
| 4,728,451 | 3/1988 | Plavac | 252/51.5 A |

*Primary Examiner*—William R. Dixon, Jr.
*Assistant Examiner*—James M. Hunter, Jr.
*Attorney, Agent, or Firm*—C. J. Caroli; R. C. Gaffney

[57] ABSTRACT

Disclosed are alkylphenyl poly(oxyalkylene) aminocarbamates having at least one basic nitrogen and an average molecular weight of about 800 to 6,000 and wherein the alkyl group contains at least 40 carbon atoms. Also disclosed are lubricating oil compositions and concentrates containing said alkylphenyl poly(oxyalkylene) aminocarbamates.

20 Claims, No Drawings

LUBRICATING OIL COMPOSITIONS CONTAINING VERY LONG CHAIN ALKYLPHENYL POLY (OXYALKYLENE) AMINOCARBAMATES

BACKGROUND OF THE INVENTION

1. Field of the Invention

This invention is directed toward dispersants compatible in lubricating oil. In particular, this invention is directed toward dispersant additives possessing improved compatibility in lubricating oil which are alkylphenyl poly(oxyalkylene) aminocarbamates having at least one basic nitrogen and wherein the alkyl group of said alkylphenyl poly(oxyalkylene) aminocarbamate contains at least 40 carbon atoms.

The incompatibility of certain dispersant additives in lubricating oil, i.e., oils which contain other additives, is recognized in the art and arises in spite of the fact that certain of these additives are known lubricating oil dispersants.

Several theories exist as to the cause of the lubricating oil incompatibility of certain additives. Without being limited to any theory, it is possible that some of these additives interfere with other additives contained in the lubricating oil and either counterbalance the effectiveness of these additives or actually cause dissolution of one or more of these additives, including possibly the dispersant additive itself.

In another theory, it is possible that the additive will decompose in the lubricating during engine operation and the decomposition products are what cause increased crankcase deposits.

In still another theory, it is also possible that the incompatibility of the additive is related to its oil solubility.

Lubricating oil incompatible additives are less than desirable insofar as their use during engine operation will result in increased crankcase deposits, i.e., varnish and sludge, in the crankcase as measured by Sequence V-D engine tests. This problem can be severe.

The instant invention is directed to a novel class of very long chain alkylphenyl poly(oxyalkylene) aminocarbamates which provide improved compatibility in lubricating oil compositions. The novel additives of this invention are alkylphenyl poly(oxyalkylene) aminocarbamates having a molecular weight of about 800 to 6,000 wherein the alkyl group of said alkylphenyl poly(oxyalkylene) aminocarbamate contains at least 40 carbon atoms.

2. Prior Art

Numerous references disclose $C_1$ to $C_{30}$ hydrocarbyl poly(oxyalkylene) aminocarbamates as fuel additives. These include the following U.S. Pat. Nos.:

| | | |
|---|---|---|
| 4,160,648; | 4,243,798; | 4,521,610; and |
| 4,191,537; | 4,270,930; | 4,568,358. |
| 4,197,409; | 4,274,837; | |
| 4,236,020; | 4,288,612; | |

Of particular relevance is U.S. Pat. No. 4,274,837 which discloses that hydrocarbyl poly(oxyalkylene) aminocarbamates containing certain poly(oxyalkylene) chains, i.e., oxypropylene, when used in fuels employed in combination with certain lubricating oils, produce crankcase varnish. This reference further discloses that lubricating oil compatible hydrocarbyl poly(oxypropylene) aminocarbamates are improved by employing the poly(oxypropylene) as a 1 to 5 $C_9$ to $C_{30}$ oxyalkylene units.

U.S. Pat. No. 4,160,648 discloses an intake system deposit control additive for fuels which is a hydrocarbyl poly(oxyalkylene) aminocarbamate wherein the hydrocarbyl group is from 1 to 30 carbon atoms including alkyl or alkylphenyl groups. Specifically disclosed hydrocarbyl groups include tetrapropenylphenyl, olelyl and a mixture of $C_{16}$, $C_{18}$ and $C_{20}$ alkyl groups. Likewise, U.S. Pat. No. 4,288,612 discloses deposit control additives for gasoline engines which are hydrocarbyl poly(oxyalkylene) aminocarbamates wherein the hydrocarbyl group contains from 1 to about 30 carbon atoms including alkylphenyl groups wherein the alkyl group is straight or branched chain of from 1 to about 24 carbon atoms. U.S. Pat. No. 4,568,358 discloses diesel fuel compositions containing an additive such as a hydrocarbyl poly(oxyalkylene) aminocarbamate. This reference discloses hydrocarbyl groups such as alkyl groups of 1 to 30 carbon atoms; aryl groups of 6 to 30 carbon atoms, alkaryl groups of 7 to 30 carbon atoms, etc.

U.S. Pat. No. 4,332,595 discloses hydrocarbyl poly(oxyalkylene) polyamines wherein the hydrocarbyl group is a hydrocarbyl radical of 8 to 18 carbon atoms derived from linear primary alcohols.

U.S. Pat. Nos. 4,233,168 and 4,329,240 among others disclose lubricating oil compositions containing a dispersant amount of a hydrocarbyl poly(oxyalkylene) aminocarbamate.

While these prior art references disclose $C_1$ to $C_{30}$ hydrocarbyl poly(oxyalkylene) aminocarbamates, none of these references disclose the unique alkylphenyl group of this invention nor do any of these references suggest that use of this unique alkylphenyl group would provide improved compatibility in lubricating oil compositions.

SUMMARY OF THE INVENTION

The instant invention is directed toward a novel class of alkylphenyl poly(oxyalkylene) aminocarbamates which possess improved compatibility with lubricating oil compositions. In particular, the instant invention is directed toward an alkylphenyl poly(oxyalkylene) aminocarbamate having at least one basic nitrogen and an average molecular weight of about 800 to 6,000 and wherein the alkyl group of said alkylphenyl poly(oxyalkylene) aminocarbamate contains at least 40 carbon atoms and the poly(oxyalkylene) polymer is derived from $C_2$ to $C_5$ oxyalkylene units with the proviso that if the poly(oxyalkylene) polymer is a homopolymer of oxyethylene then the poly(oxyethylene) polymer does not contain more than 25 oxyethylene units. The instant invention is based on the discovery that use of the unique alkylphenyl group, i.e., an alkylphenyl group wherein the alkyl group contains at least 40 carbon atoms, imparts to the alkylphenyl poly(oxyalkylene) aminocarbamate improved lubricating oil compatibility.

The compounds of this invention are useful dispersants in lubricating oil. Thus, in its composition aspect, the instant invention is directed toward a lubricating oil composition comprising an oil of lubricating viscosity and a dispersant effective amount of an alkylphenyl poly(oxyalkylene) aminocarbamate of this invention.

DETAILED DESCRIPTION OF THE INVENTION

The alkylphenyl poly(oxyalkylene) aminocarbamates of the present invention consist of an amino moiety and an alkylphenyl poly(oxyalkylene) polymer bonded through a carbamate linkage, i.e., —OC(O)N<. The specific alkylphenyl group employed in the instant invention in the alkylphenyl poly(oxyalkylene) polymer is critical to achieving improved lubricating oil compatibility for the alkylphenyl poly(oxyalkylene) aminocarbamates. In particular, it has been found that employing the alkylphenyl group of this invention wherein the alkyl group contains at least 40 carbon atoms results in an alkylphenyl poly(oxyalkylene) aminocarbamate which has improved lubricating oil compatibility.

The Preferred Alkylphenyl Group

The preferred alkylphenyl group of the alkylphenyl poly(oxyalkylene) aminocarbamate employed in this invention is derived from the corresponding alkylphenol of Formula I below:

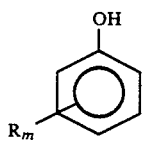

wherein R is an alkyl group of at least 40 carbon atoms and m is an integer from 1 to 2.

Preferably, m is one.

Preferably, R is an alkyl group of from 50 to 200 carbon atoms. More preferably, R is an alkyl group of from 60 to 100 carbon atoms.

When m is one, the alkylphenyl is a monoalkylphenyl; whereas when m is two, the alkylphenyl is a dialkylphenyl.

The alkylphenols of Formula I above are prepared by reacting the appropriate olefin or olefin mixture with phenol in the presence of an alkylating catalyst at a temperature of from about 60° C. to 200° C., and preferably 125° C. to 180° C. either neat or in an essentially inert solvent at atmospheric pressure. Preferred alkylating catalysts are a sulfonic acid catalyst such as Amberlyst 15 ® available from Rohm and Haas, Philadelphia, Pa. or boron trifluoride (or an etherate of boron trifluoride). Molar ratios of reactants can be employed. When molar ratios are employed, the reaction yields a mixture of dialkylphenol, monoalkylphenol and unreacted phenol. As noted above, dialkylphenol and monoalkylphenol can be used to prepare the additives used in the compositions of this invention whereas the unreacted phenol is preferably removed from the post reaction mixture via conventional techniques. Alternatively, molar excess of phenol can be employed, i.e., 2 to 2.5 equivalents of phenol for each equivalent of olefin with unreacted phenol recycled. The latter process maximizes monoalkylphenol. Examples of inert solvents include benzene, toluene, chlorobenzene and 250 thinner which is a mixture of aromatics, paraffins and naphthenes.

Particularly preferred alkylphenols employed in this invention are monoalkylphenols represented by Formula II below:

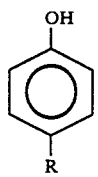

wherein R is as defined above.

A particularly preferred class of olefins for use in preparing alkylphenols useful in this invention are polyolefin polymers. Polyolefin polymers are polymers comprising a major amount of $C_2$ to $C_5$ mono-olefin, e.g., ethylene, propylene, butylene, isobutylene and pentene. The polymers can be homopolymers such as polyisobutylene as well as copolymers of two or more such olefins such as copolymers of: ethylene and propylene, butylene, and isobutylene, etc. Other copolymers include those in which a minor amount of the copolymer monomers, e.g., 1 to 20 mole percent is a $C_4$ to $C_8$ nonconjugated diolefin, e.g., a copolymer of isobutylene and butadiene or a copolymer of ethylene, propylene and 1,4-hexadiene, etc.

The polyolefin polymer usually contains at least 40 carbon atoms, although preferably 50 to 200 carbon atoms and more preferably 60 to 100 carbon atoms.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as U.S. Pat. No. 3,912,764. The above are incorporated by reference for their disclosures of suitable polybutenes.

In addition to the reaction of a polyolefin with phenol, many other alkylating hydrocarbons may likewise be used with phenol to produce alkylphenol. Other suitable alkylating hydrocarbons include cyclic, linear, branched and internal or alpha olefins having molecular weights of at least about 560. For example, alpha olefins obtained from the ethylene growth process gives even number carbon olefins. Another source of olefins is by the dimerization of alpha olefins over an appropriate catalyst such as the well-known Ziegler catalyst. Internal olefins are easily obtained by the isomerization of alpha olefins over a suitable catalyst such as silica.

Preferred Poly(oxyalkylene) Component

The alkylphenyl poly(oxyalkylene) polymers which are utilized in preparing the carbamates of the present invention are monohydroxy compounds, i.e., alcohols, often termed alkylphenyl "capped" poly(oxyalkylene) glycols and are to be distinguished from the poly(oxyalkylene) glycols (diols), which are not alkylphenyl terminated, i.e., not capped. The alkylphenyl poly(oxyalkylene) alcohols are produced by the addition of lower alkylene oxides, such as ethylene oxide, propylene oxide, the butylene oxides, or the pentylene oxides to the alkylphenol of Formula I, i.e.,

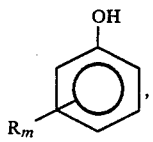 I under polymerization conditions, wherein R and m are as defined above. Preferred poly(oxyalkylene) polymers are those derived from $C_3$ to $C_4$ oxyalkylene units; more preferably $C_3$ oxypropylene units. Methods of production and properties of these polymers are disclosed in U.S. Pat. Nos. 2,841,479 and 2,782,240 and Kirk-Othmer's "Encyclopedia of Chemical Technology", Volume 19, p. 507. In the polymerization reaction, a single type of alkylene oxide may be employed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention.

Homopolymers of poly(oxyethylene) polymers are much more hydrophilic than homopolymers of $C_3$–$C_5$ poly(oxyalkylene) polymers. Accordingly, when homopolymers of poly(oxyethylene) polymers are employed, the amount of poly(oxyethylene) must be limited so as to ensure fuel solubility and lubricating oil compatibility of the final carbamate. In general, this is accomplished by limiting the poly(oxyethylene) polymer to about 25 oxyethylene units or less; although preferably about 10 oxyethylene units or less; and most preferably about 5 oxyethylene units or less.

Likewise, copolymers containing a mixture of oxyethylene units and $C_3$–$C_5$ oxyalkylene units are formulated to ensure that the copolymer possesses lubricating oil compatibility.

In general, the poly(oxyalkylene) polymers are mixtures of compounds that differ in polymer chain length. However, their properties closely approximate those of the polymer represented by the average composition and molecular weight.

In general, the very long chain alkylphenyl terminating group on the alkylphenyl poly(oxyalkylene) aminocarbamates of this invention allow for use of less oxyalkylene units in the poly(oxyalkylene) polymer to ensure lubricating oil compatibility than are necessary in prior art carbamate fuel additives. Accordingly, while longer poly(oxyalkylene) polymers are functional in this invention, such longer polymers are not necessary. Therefore, each poly(oxyalkylene) polymer utilized in this invention contains at least 1 oxyalkylene unit, preferably from 1 to about 100 oxyalkylene units, more preferably from about 1 to about 25 oxyalkylene units, even more preferably from about 1 to about 10 oxyalkylene units, and most preferably about 5 oxyalkylene units or less. It is understood that if the poly(oxyalkylene) polymer is a homopolymer of poly(oxyethylene), the polymer length is governed by the constraints discussed above.

An alternative method for preparing alkylphenyl poly(oxyalkylene) polymers having 1, 2 or 3 oxyalkylene units involves employing a compound of Formula III below:

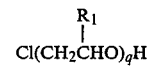 III wherein q is an integer from 1 to 3 and $R_1$ is hydrogen or a $C_1$ to $C_3$ alkyl group. When employing the compound of Formula III, the phenoxide of the alkylphenol, I, is first prepared and then reacted with the compound of Formula III to yield the desired alkylphenol poly(oxyalkylene) polymer having from 1 to 3 oxyalkylene units. Compounds of Formula III are either commercially available or can be prepared by art recognized methods.

Preferred Amine Component

The amine moiety of the alkylphenyl poly(oxyalkylene) aminocarbamate employed in this invention is preferably derived from a polyamine having from 2 to about 12 amine nitrogen atoms and from 2 to about 40 carbon atoms. The polyamine is preferably reacted with an alkylphenyl poly(oxyalkylene) chloroformate to produce the alkylphenyl poly(oxyalkylene) aminocarbamate additives finding use within the scope of the present invention. The chloroformate is itself derived from alkylphenyl poly(oxyalkylene) alcohol by reaction with phosgene. The polyamine, encompassing diamines, provides the product alkylphenyl poly(oxyalkylene) aminocarbamate with, on average, at least about one basic nitrogen atom per carbamate molecule, i.e., a nitrogen atom titratable by a strong acid. The polyamine preferably has a carbon-to-nitrogen ratio of from about 1:1 to about 10:1.

The polyamine may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms. At least one of the substituents on one of the basic nitrogen atoms of the polyamine is hydrogen, e.g., at least one of the basic nitrogen atoms of the polyamine is a primary or secondary amino nitrogen atom.

Hydrocarbyl, as used in describing all the components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylene and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-(2-(2-ethoxyethoxy)ethoxy)ethyl, 3,6,9,12-tetraoxatetradecyl, 2-(2-ethoxyethoxy)hexyl, etc. The acyl groups of the aforementioned (C) substituents are such as propionyl, acetyl, etc. The more preferred substituents are hydrogen, $C_1$–$C_4$ alkyls and $C_1$–$C_4$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and poly-substituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethyl-propylene trimethylene, 1,3,2-hydroxypropylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydroxy- and hydrocarbyl-substituted polyamines. Among the polyalkylene polyamines, those containing 2–12 amine nitrogen atoms and 2–24 carbon atoms are especially preferred, e.g., ethylene diamine, propylene diamine, butylene diamine, pentylene diamine, hexylene diamine, diethylene triamine and dipropylene triamine, and the $C_2$–$C_3$ alkylene polyamines are most preferred, in particular, the lower polyalkylene polyamines, e.g., ethylene diamine, diethylene triamine, propylene diamine, dipropylene triamine, etc.

The amine component of the alkylphenyl poly(oxyalkylene) aminocarbamate also may be derived from heterocyclic polyamines, heterocyclic substituted amines and substituted heterocyclic compounds, wherein the heterocycle comprises one or more 5–6 membered rings containing oxygen and/or nitrogen. Such heterocycles may be saturated or unsaturated and substituted with groups selected from the aforementioned (A), (B), (C) and (D). The heterocycles are exemplified by piperazines, such as 2-methylpiperazine, N-(2-hydroxyethyl)piperazine, 1,2-bis-(N-piperazinyl)ethane, and N,N'-bis(N-piperazinyl)piperazine, 2-methylimidazoline, 3-aminopiperidine, 2-aminopyridine, 2-(3-aminoethyl)-3-pyrroline, 3-aminopyrrolidine, N-(3-aminopropyl)-morpholine, etc. Among the heterocyclic compounds, the piperazines are preferred.

Another class of suitable polyamines are diaminoethers represented by Formula IV $$H_2N-X_1-(OX_2)_r-NH_2 \qquad IV$$

wherein $X_1$ and $X_2$ are independently alkylene from 2 to about 5 carbon atoms and r is an integer from 1 to about 10. Diamines of Formula IV are disclosed in U.S. Pat. No. 4,521,610, which is incorporated herein by reference for its teaching of such diamines.

Typical polyamines that can be used to form the compounds of this invention by reaction with a poly(oxyalkylene)chloroformate include the following: ethylene diamine, 1,2-propylene diamine, 1,3-propylene diamine, diethylene triamine, triethylene tetramine, hexamethylene diamine, tetraethylene pentamine, dimethylaminopropylene diamine, N-(beta-aminoethyl)piperazine, N-(beta-aminoethyl)piperidine, 3-amino-N-ethylpiperidine, N-(beta-aminoethyl)morpholine, N,N'-di(beta-aminoethyl)piperazine, N,N'-di(beta-aminoethylimidazolidone-2; N-(beta-cyanoethyl)ethane-1,2-diamine, 1-amino-3,6,9-triazaoctadecane, 1-amino-3,6-diaza-9-oxadecane, N-(beta-aminoethyl)diethanolamine, N'-acetyl-N'-methyl-N-(beta-aminoethyl)ethane-1,2-diamine, N-acetonyl-1,2-propanediamine, N-(beta-nitroethyl)-1,3-propane diamine, 1,3-dimethyl-5-(beta-aminoethyl)hexahydrotriazine, N-(beta-aminoethyl)-hexahydrotriazine, 5-(beta-aminoethyl)-1,3,5-dioxazine, 2-(2-aminoethylamino)-ethanol, 2[2-(2-aminoethylamino)ethylamino]-ethanol.

The amine component of the alkylphenyl poly(oxyalkylene) aminocarbamate may also be derived from an amine-containing compound which is capable of reacting with an alkylphenyl poly(oxyalkylene) alcohol to produce an alkylphenyl poly(oxyalkylene) aminocarbamate having at least one basic nitrogen atom. For example, a substituted aminoisocyanate, such as $(R_3)_2NCH_2CH_2NCO$, wherein $R_3$ is, for example, a hydrocarbyl group, reacts with the alcohol to produce the aminocarbamate additive finding use within the scope of the present invention. Typical aminoisocyanates that may be used to form the fuel additive compounds of this invention by reaction with a hydrocarbylpoly(oxyalkylene) alcohol include the following: N,N-(dimethyl)aminoisocyanatoethane, generally, N,N-(dihydrocarbyl)aminoisocyanatoalkane, more generally, N-(perhydrocarbyl)isocyanatopolyalkylene polyamine, N,N-(dimethyl)aminoisocyanatobenzene, etc.

In many instances the amine used as a reactant in the production of the carbamate of the present invention is not a single compound but a mixture in which one or several compounds, predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product. Methods of preparation of amines, isocyanates and their reactions are detailed in Sidgewick's "The Organic Chemistry of Nitrogen", Clarendon Press, Oxford, 1966; Nollers' "Chemistry of Organic Compounds", Saunders, Philadelphia, 2nd Ed. 1957; and Kirk-Othmer's "Encyclopedia of Chemical Technology", 2nd Ed., especially Volume 2, pp. 99–116.

Preferred Alkylphenyl Poly(oxyalkylene) Aminocarbamate

Having described the preferred alkylphenyl poly(oxyalkylene) component and the preferred polyamine component, the preferred alkylphenyl poly(oxyalkylene) aminocarbamate additive of the present invention is obtained by linking these components together through a carbamate linkage i.e.,

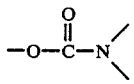

wherein the ether oxygen may be regarded as the terminal hydroxyl oxygen of the alkylphenyl poly(oxyalkylene) alcohol component, and the carbonyl group —C(O)— is preferably provided by the coupling agent, e.g., phosgene.

The alkylphenyl poly(oxyalkylene) aminocarbamate employed in the present invention has at least one basic nitrogen atom per molecule. A "basic nitrogen atom" is one that is titratable by a strong acid, e.g., a primary, secondary, or tertiary amino nitrogen, as distinguished from, for example, an amido nitrogen, i.e.,

which is not so titratable. Preferably, the basic nitrogen is in a primary or secondary amino group.

The preferred alkylphenyl poly(oxyalkylene) aminocarbamate has an average molecular weight of from about 800 to 6,000; preferably an average molecular weight of from 800 to 3,000; and most preferably an average molecular weight of from 1,000 to 2,500.

A preferred class of alkylphenyl poly(oxyalkylene) aminocarbamate can be described by the following Formula V

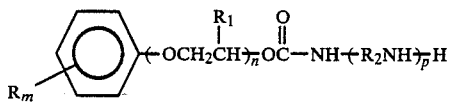

wherein R is an alkyl group containing at least 40 carbon atoms; $R_1$ is hydrogen or alkyl of 1 to 3 carbon atoms; $R_2$ is alkylene of from 2 to about 6 carbon atoms; m is an integer from 1 to 2; n is an integer such that the molecular weight of the compound is from about 800 to 6,000; and p is an integer from 1 to about 6 and with the proviso that if $R_1$ is hydrogen then n is an integer from 1 to 25.

Preparation of the Alkylphenyl Poly(oxyalkylene) Aminocarbamate

The additives employed in this invention can be most conveniently prepared by first reacting the appropriate alkylphenyl poly(oxyalkylene) alcohol with phosgene to produce an alkylphenyl poly(oxyalkylene) chloroformate. The chloroformate is then reacted with the polyamine to produce the desired alkylphenyl poly(oxyalkylene) aminocarbamate.

Preparation of aminocarbamates are disclosed in U.S. Pat. Nos. 4,160,648; 4,191,537; 4,197,409; 4,236,020; 4,243,798; 4,270,930; 4,274,837; 4,288,612; 4,512,610; and 4,568,358, which are incorporated wherein by reference. In general, the reaction of the poly(oxyalkylene) compound and phosgene is usually carried out on an essentially equimolar basis, although excess phosgene can be used to improve the degree of reaction. The reaction may be carried out a temperatures from $-10°$ to 100° C., preferably in the range of 0° to 50° C. The reaction will usually be complete within ¼ to 5 hours. Times of reaction will usually be in the range of from 2 to 4 hours.

A solvent may be used in the chloroformylation reaction. Suitable solvents include benzene, toluene, etc.

The reaction of the resultant chloroformate with the amine may be carried out neat or preferably in solution. Temperatures of from $-10°$ to 200° C. may be utilized, the desired product may be obtained by water wash and stripping usually be the aid of vacuum, of any residual solvent.

The mol ratio of polyamine to polyether chloroformate will generally be in the range from about 2 to 20 mols of polyamine per mol of chloroformate, and more usually 5 to 15 mols of polyamine per mole of chloroformate. Since suppression of polysubstitution of the polyamino is usually desired, large molar excesses of the polyamine will be used. Additionally, the desired adduct is the monocarbamate compound, as opposed to the bis(carbamate) or disubstituted aminoether.

The reaction or reactions may be conducted with or without the presence of a reaction solvent. A reaction solvent is generally employed whenever necessary to reduce the viscosity of the reaction product. These solvents should be stable and inert to the reactants and reaction product. Depending on the temperature of the reaction, the particular chloroformate used, the mol ratios, as well as the reactant concentrations, the reaction time may vary from less than 1 minute to 3 hours.

After the reaction has been carried out for a sufficient length of time, the reaction mixture may be subjected to extraction with a hydrocarbon-water or hydrocarbon-alcohol-water medium to free the product from any low-molecular-weight amine salts which have formed and any unreacted diamine. The product may then be isolated by evaporation of the solvent. Further purification may be effected by column chromatography on silica gel.

Depending on the particular application of the composition of this invention, the reaction may be carried out in the medium in which it will ultimately find use, e.g., polyether carriers or an oleophilic organic solvent or mixtures thereof and be formed at concentrations which provide a concentrate of a detergent composition. Thus, the final mixture may be in a form to be used directly for blending in fuels.

An alternative process for preparing the alkylphenyl poly(oxyalkylene) aminocarbamates employed in this invention involves the use of an arylcarbonate intermediate. That is to say, the alkylphenyl poly(oxyalkylene) alcohol is reacted with an aryl chloroformate to form an arylcarbonate which is then reacted with the polyamine to form the aminocarbamate employed in this invention. Particularly useful aryl chloroformates include phenyl chloroformate, p-nitrophenyl chloroformate, 2,4-dinitrophenyl chloroformate, p-chlorophenyl chloroformate, 2,4-dichlorophenyl chloroformate, and p-trifluoromethylphenyl chloroformate. Use of the aryl carbonate intermediate allows for conversion to aminocarbamates containing close to the theoretical basic nitrogen while employing less excess of polyamine, i.e., molar ratios of generally from 1:1 to about 5:1 of polyamine to the arylcarbonate, and additionally avoids the generation of hydrogen chloride in the reaction forming the aminocarbamate. Preparation of hydrocarbyl capped poly(oxyalkylene) aminocarbamates via an arylcarbonate intermediate are disclosed in U.S. Ser. Nos.

586,533 and 689,616, which are incorporated herein by reference.

Also included within the scope of this invention are fully formulated lubricating oils containing a dispersant effective amount of an alkylphenyl poly(oxyalkylene) aminocarbamate. Contained in the fully formulated composition is:

1. an alkenyl succinimide,
2. a Group II metal salt of a dihydrocarbyl dithiophosphoric acid,
3. a neutral or overbased alkali or alkaline earth metal hydrocarbyl sulfonate or mixtures thereof, and
4. a neutral or overbased alkali or alkaline earth metal alkylated phenate or mixtures thereof.
5. A viscosity index (VI) improver.

The alkenyl succinimide is present to act as a dispersant and prevent formation of deposits formed during operation of the engine. The alkenyl succinimides are well-known in the art. The alkenyl succinimides are the reaction product of a polyolefin polymer-substituted succinic anhydride with an amine, preferably a polyalkylene polyamine. The polyolefin polymer-substituted succinic anhydrides are obtained by reaction of a polyolefin polymer or a derivative thereof with maleic anhydride. The succinic anhydride thus obtained is reacted with the amine compound. The preparation of the alkenyl succinimides has been described many times in the art. See, for example, U.S. Pat. Nos. 3,390,082; 3,219,666; and 3,172,892, the disclosure of which are incorporated herein by reference. Reduction of the alkenyl substituted succinic anhydride yields the corresponding alkyl derivative. The alkyl succinimides are intended to be included within the scope of the term "alkenyl succinimide". A product comprising predominantly mono- or bis-succinimide can be prepared by controlling the molar ratios of the reactants. Thus, for example, if one mole of amine is reacted with one mole of the alkenyl or alkyl substituted succinic anhydride, a predominantly mono-succinimide product will be prepared. If two moles of the succinic anhydride are reacted per mole of polyamine, a bis-succinimide will be prepared.

Particularly good results are obtained with the lubricating oil compositions of this invention when the alkenyl succinimide is a polyisobutene-substituted succinic anhydride of a polyalkylene polyamine.

The polyisobutene from which the polyisobutene-substituted succinic anhydride is obtained by polymerizing isobutene can vary widely in its compositions. The average number of carbon atoms can range from 30 or less to 250 or more, with a resulting number average molecular weight of about 400 or less to 3,000 or more. Preferably, the average number of carbon atoms per polyisobutene molecule will range from about 50 to about 100 with the polyisobutenes having a number average molecular weight of about 600 to about 1,500. More preferably, the average number of carbon atoms per polyisobutene molecule ranges from about 60 to about 90, and the number average molecular weight ranges from about 800 to 1,300. The polyisobutene is reacted with maleic anhydride according to well-known procedures to yield the polyisobutene-substituted succinic anhydride.

In preparing the alkenyl succinimide, the substituted succinic anhydride is reacted with a polyalkylene polyamine to yield the corresponding succinimide. Each alkylene radical of the polyalkylene polyamine usually has from 2 up to about 8 carbon atoms. The number of alkylene radicals can range up to about 8. The alkylene radical is exemplified by ethylene, propylene, butylene, trimethylene, tetramethylene, pentamethylene, hexamethylene, octamethylene, etc. The number of amino groups generally, but not necessarily, is one greater than the number of alkylene radicals present in the amine, i.e., if a polyalkylene polyamine contains 3 alkylene radicals, it will usually contain 4 amino radicals. The number of amino radicals can range up to about 9. Preferably, the alkylene radical contains from about 2 to about 4 carbon atoms and all amine groups are primary or secondary. In this case, the number of amine groups exceeds the number of alkylene groups by 1. Preferably the polyalkylene polyamine contains from 3 to 5 amine groups. Specific examples of the polyalkylene polyamines include ethylenediamine, diethylenetriamine, triethylenetetramine, propylenediamine, tripropylenetetramine, tetraethylenepentamine, trimethylenediamine, pentaethylenehexamine, di-(trimethylene)triamine, tri(hexamethylene)tetramine, etc.

Other amines suitable for preparing the alkenyl succinimide useful in this invention include the cyclic amines such as piperazine, morpholine and dipiperazines.

Preferably the alkenyl succinimides used in the compositions of this invention have the following formula

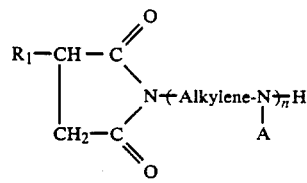

wherein:
(a) $R_1$ represents an alkenyl group, preferably a substantially saturated hydrocarbon prepared by polymerizing aliphatic monoolefins. Preferably $R_1$ is prepared from isobutene and has an average number of carbon atoms and a number average molecular weight as described above;
(b) the "Alkylene" radical represents a substantially hydrocarbyl group containing from 2 up to about 8 carbon atoms and preferably containing from about 2–4 carbon atoms as described hereinabove;
(c) A represents a hydrocarbyl group, an amine-substituted hydrocarbyl group, or hydrogen. The hydrocarbyl group and the amine-substituted hydrocarbyl groups are generally the alkyl and amino-substituted alkyl analogs of the alkylene radicals described above. Preferably A represents hydrogen;
(d) n represents an integer of from 1 to about 8, and preferably from about 3–5.

Also included within the term alkenyl succinimide are the modified succinimides which are disclosed in U.S. Pat. No. 4,612,132 which is incorporated herein by reference.

The alkenyl succinimide is present in the lubricating oil compositions of the invention in an amount effective to act as a dispersant and prevent the deposit of contaminants formed in the oil during operation of the engine. The amount of alkenyl succinimide can range from about 1 percent to about 20 percent weight of the total lubricating oil composition. Preferably the amount of alkenyl succinimide present in the lubricating oil composition of the invention ranges from about 1 to about 10 percent by weight of the total composition.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well-known in the art. The hydrocarbyl group must have a sufficient number of carbon atoms to render the sulfonate molecule oil soluble. Preferably, the hydrocarbyl portion has at least 20 carbon atoms and may be aromatic or aliphatic, but is usually alkylaromatic. Most preferred for use are calcium, magnesium or barium sulfonates which are aromatic in character.

Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

The sulfonates may be neutral or overbased having base numbers up to about 400 or more. Carbon dioxide and calcium hydroxide or oxide are the most commonly used material to produce the basic or overbased sulfonates Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols. One of the functions of the phenates is to act as a detergent and dispersant. Among other things, it prevents the deposition of contaminants formed during high temperature operation of the engine. The phenols may be mono- or polyalkylated.

The alkyl portion of the alkyl phenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material. Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, tricontyl, and the like. Other suitable synthetic sources of the alkyl radical include olefin polymers such as polypropylene, polybutylene, polyisobutylene and the like.

The alkyl group can be straight-chained or branch-chained, saturated or unsaturated (if unsaturated, preferably containing not more than 2 and generally not more than 1 site of olefinic unsaturation). The alkyl radicals will generally contain from 4 to 30 carbon atoms. Generally when the phenol is monoalkyl-substituted, the alkyl radical should contain at least 8 carbon atoms. The phenate may be sulfurized if desired. It may be either neutral or overbased and if overbased will have a base number of up to 200 to 300 or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2 to 13% by weight of the total composition. Most preferably, the overbased phenates are present from 0.2% to 5% by weight of the total composition. Preferred metals are calcium, magnesium, strontium or barium.

The sulfurized alkaline earth metal alkyl phenates are preferred. These salts are obtained by a variety of processes such as treating the neutralization product of an alkaline earth metal base and an alkylphenol with sulfur. Conveniently the sulfur, in elemental form, is added to the neutralization product and reacted at elevated temperatures to produce the sulfurized alkaline earth metal alkyl phenate.

If more alkaline earth metal base were added during the neutralization reaction than was necessary to neutralize the phenol, a basic sulfurized alkaline earth metal alkyl phenate is obtained. See, for example, the process of Walker et al, U.S. Pat. No. 2,680,096. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol.

Carbon dioxide and calcium hydroxide or oxide are the most commonly used material to produce the basic or "overbased" phenates. A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, columns 6 and 7, wherein these compounds and their preparation are described generally. Suitably, the Group II metal salts of the dihydrocarbyl dithiophosphoric acids useful in the lubricating oil composition of this invention contain from about 4 to about 12 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec.-butyl, hexyl, isohexyl, octyl, 2-ethylhexyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

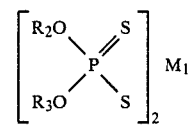

wherein (e) $R_2$ and $R_3$ each independently represent hydrocarbyl radicals as described above, and (f) $M_1$ represents a Group II metal cation as described above.

The dithiophosphoric salt is present in the lubricating oil compositions of this invention in an amount effective to inhibit wear and oxidation of the lubricating oil. The amount ranges from about 0.1 to about 4 percent by weight of the total composition, preferably the salt is present in an amount ranging from about 0.2 to about 2.5 percent by weight of the total lubricating oil composition. The final lubricating oil composition will ordinarily contain 0.025 to 0.25% by weight phosphorus and preferably 0.05 to 0.15% by weight.

Viscosity index (VI) improvers are either non-dispersant or dispersant VI improvers. Non-dispersant VI improvers are typically hydrocarbyl polymers including copolymers and terpolymers. Typically hydrocarbyl copolymers are copolymers of ethylene and propylene. Such non-dispersant VI improvers are disclosed in U.S. Pat. Nos. 2,700,633; 2,726,231; 2,792,288; 2,933,480; 3,000,866; 3,063,973; and 3,093,621 which are incorporated herein by reference for their teaching of non-dispersant VI improvers.

Dispersant VI improvers can be prepared by functionalizing non-dispersant VI improvers. For example, non-dispersant hydrocarbyl copolymer and terpolymer VI improvers can be functionalized to produce aminated oxidized VI improvers having dispersant properties and a number average molecular weight of from 1,500 to 20,000. Such functionalized dispersant VI improvers are disclosed in U.S. Pat. Nos. 3,864,268; 3,769,216; 3,326,804 and 3,316,177 which are incorporated herein by reference for their teaching of such dispersant VI improvers.

Other dispersant VI improvers include amine-grafted acrylic polymers and copolymers wherein one monomer contains at least one amino group. Typical compositions are described in British Pat. No. 1,488,382; and U.S. Pat. Nos. 4,89,794 and 4,025,452, which are incorporated herein by reference for their teaching of such dispersant VI improvers.

Non-dispersant and dispersant VI improvers are generally employed at from 5 to 20 percent by weight in the lubricating oil composition.

Lubricating Oil Compositions

The alkylphenyl poly(oxyalkylene) aminocarbamates of this invention are useful as dispersant additives when employed in lubricating oils. When employed in this manner, the additive is usually present in from 0.2 to 10 percent by weight to the total composition, preferably at about 0.5 to 8 percent by weight and more preferably at about 1 to 6 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. The concentrates of this invention usually include from about 90 to 50 weight percent of an oil of lubricating viscosity and from about 10 to 50 weight percent of the additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

The following examples are offered to specifically illustrate this invention. These examples and illustrations are not to be construed in any way as limiting the scope of this invention.

EXAMPLES

Example 1

Preparation of $C_{65}$ to $C_{70}$ Alkylphenyl Poly(oxypropylene) Alcohol

To a dried 5-liter, 3-neck flask under a nitrogen atmosphere was added 1.5 liters of dry toluene and 1125 grams H-100 ® (an alkylphenol, prepared from polybutene-24, having a hydroxyl number of approximately 34, and a number average of approximately 65–70 carbon atoms in the alkyl portion of the alkylphenol. H-100 ® alkylphenol also contains approximately one-third (⅓) inactive compounds. H-100 ® alkylphenol is available from Amoco Petroleum Additives Company, Clayton, Mo.). The system was warmed to approximately 60° C. and 5.5 grams (0.14 moles) of metallic potassium cut into small pieces was slowly added with vigorous stirring. The temperature of the reaction system was allowed to increase during this addition and reached approximately 105° C. After 2½ hours, all of the metallic potassium was dissolved. The reaction system was then allowed to cool to 40° C. Afterwards, 131.5 grams (about 5 equivalents per equivalent of alkylphenol) of propylene oxide was added to the system by an addition funnel at an addition rate slow enough to avoid flooding of the vapor condensing system. The system was then gently refluxed for 13 hours at which point the temperature increased to 113° C. and was held there for an addition 3.5 hours. The system was then cooled to 60° C. and the reaction quenched by the addition of 0.075 liter of 2N HCl solution. The system was then dried by azeotropic distillation to yield a toluene solution of the crude product. The system was then diluted with 1 liter of toluene.

Example 2

Preparation of $C_{65}$ to $C_{70}$ Alkylphenyl Poly(oxypropylene) Chloroformate The toluene solution containing the product of Example 1 above in a 5-liter, 3-neck flask under a nitrogen atmosphere was cooled to about 5° C. with stirring. While stirring, 301 grams of a 20% solution of phosgene in toluene was added all at once to the reaction system. The reaction system was allowed to warm to room temperature and stirred gently for 24 hours. In order to remove excess phosgene as well as HCl formed during the reaction, the system was vigorously sparged with nitrogen. After completion of the reaction, an infrared analysis of an aliquot revealed a strong chloroformate absorption at 1785 cm$^{-1}$ and no detectable alcohol absorption at 3450 cm$^{-1}$.

Example 3

Preparation of $C_{65}$ to $C_{70}$ Alkylphenyl Poly(oxypropylene) Ethylene Diamine Carbamate The entire chloroformate/toluene solution of Example 2 was diluted with 4 liters of dry toluene. In a separate flask, 487 grams of ethylene diamine (8.1 moles) approximately 20 equivalents per equivalent of chloroformate, was also diluted with 4 liters of dry toluene. At room temperature, these two solutions were rapidly mixed using two variable speed Teflon gear pumps and a 10-inch Kenics static mixer. After fifteen minutes, the crude reaction mixture was stripped, diluted with 10 liters of hexane, and washed successively once with water and three times with a slightly basic (pH $\approx$ 9) brine solution. Phase separation of the aqueous brine solution and the hexane solution was improved by adding isopropanol as needed. The hexane solution was separated, dried over anhydrous sodium sulfate, filtered and stripped to afford the title product as a thick orange liquid having an alkalinity value of 17.7 and 0.44 weight percent basis nitrogen.

Example 4

Preparation of $C_{65}$ to $C_{70}$ Alkylphenyl Poly(oxypropylene) Diethylene Triamine Carbamate In the manner described in Example 3 above, a $C_{65}$ to $C_{70}$ alkylphenyl poly(oxypropylene) chloroformate (prepared from 1168 grams of H-100® alkylphenol) prepared similarly to the method in Examples 1 and 2 above was treated with 814 grams of diethylene triamine (7.89 moles) approximately 20 equivalents of diethylene triamine per equivalent of chloroformate to afford the title compound having an alkalinity value of 25.7 and 0.64 weight percent basic nitrogen.

REFERENCE EXAMPLE A

Preparation of Tetrapropenylphenol

To a 2-liter flask, equipped with stirrer, Dean Stark trap, condensor, and nitrogen inlet and outlet was added 567 grams of tetrapropylene, 540 grams of phenol, 72 grams of a sulfonic acid cation exchange resin (polystyrene cross-linked with divinylbenzene) catalyst (Amberlyst 15 ® available from Rohm and Haas, Philadelphia, Pa.). The reaction mixture was heated to about 110° C. for about 3 hours with stirring under a nitrogen atmosphere. The reaction mixture was stripped by heating under vacuum and the resulting product filtered hot over diatomaceous earth to afford 626 grams of tetrapropenylphenol and with a hydroxyl number of 205 and with 96% para-alkylphenol content.

Reference alkylphenyl poly(oxyalkylene) aminocarbamates were prepared from the tetrapropenyl alkylphenol of Reference Example A in a manner similar to Examples 1-4 above. Reference Examples B through D found in Table I below summarizes the different tetrapropenyl poly(oxyalkylene) aminocarbamates so prepared.

TABLE I

COMPOUNDS OF THE FORMULA $$R_3O\text{-}(CH_2CHO)_{\overline{n}}\overset{R_1}{\underset{|}{C}}\overset{O}{\underset{\|}{N}}NH\text{-}(R_2\text{-}NH)_{\overline{p}}H$$

| Example | $R_3$ | $R_1$ | $R_2$ | n | p |
|---|---|---|---|---|---|
| B | tetrapropenylphenyl | $-C_2H_5$ | $-CH_2CH_2-$ | 17 | 1 |
| C | tetrapropenylphenyl | $-CH_3$ | $-CH_2CH_2-$ | 20 | 1 |
| D | tetrapropenylphenyl | $-CH_3$ | $-CH_2CH_2-$ | 5 | 1 |
| 3 | $C_{65}$ to $C_{70}$ alkylphenyl | $-CH_3$ | $-CH_2CH_2-$ | 5 | 1 |
| 4 | $C_{65}$ to $C_{70}$ alkylphenyl | $-CH_3$ | $-CH_2CH_2-$ | 5 | 2 |

Example 5

Oil Solubility Bench Test

This procedure was designed to determine the oil solubility/compatibility of different additives in a fully formulated lubricating oil. Insofar as up to 25-30% of a gasoline additive can enter into the crankcase via "blow-by" and/or cylinder wall/piston ring "wipe down", this is an important performance criteria.

The lubricating oil composition was formulated to contain: 6 percent by weight of a mono-polyisobutenyl succinimide; 20 millimoles per kilogram of a highly overbased sulfurized calcium phenate; 30 millimoles per kilogram of a highly overbased sulfurized calcium hydrocarbyl sulfonate; 22.5 millimoles per kilogram of a zinc dithiophosphate; 13 weight percent of a commercial non-dispersant $C_2$-$C_3$ copolymer viscosity index improver; parts per million of a foam inhibitor in 150N Exxon base oil to give a 10 W 40 formulated oil.

The oil solubility of the additive was determined as follows:

To a heated solution (50 grams) of the above-described fully formulated lubricating oil was added 50 grams of the neat additive. The mixture was then heated with constant stirring to 170° F. and maintained at that temperature for 15 minutes. Dilutions were then prepared according to the desired solubility test range using fresh hot reference oil as the diluent. In each case, the diluted samples were stirred to 170° F. for 10 minutes to insure complete mixing. The solutions were then sealed and left to cool undisturbed for from 1-5 days typically at room temperature. Each sample was then rated visually for oil continuity.

Additives that were marginally soluble in this blend separated as a denser secondary phase, and were clearly visible as such without the need for centrifugation. Additives which gave rise to oil incompatibility problems were inherently oil soluble, however, they tended to displace what appears to be the VI improver. This phenomenon resulted in the separation of the VI improver which is less dense than the bulk oil forming a clear thick upper layer. The solubility/compatibility of a gasoline additive was thereby defined as the highest concentration (on a weight basis) which did not result in the formation of either an insoluble lower additive phase or an insoluble upper VI improver phase.

Table II below contains compatibility data for the hydrocarbyl poly(oxyalkylene) aminocarbamate. Oil compatibility is reported weight percent of additive in the lubricating oil composition.

TABLE II

| Example | Oil Compatibility (Wt. %) |
|---------|---------------------------|
| 3 | 50 |
| 4 | 50 |
| B | 15 |
| C | 7 |
| D | 11 |

The above data demonstrates that the additives of the instant invention possess improved oil compatibility as compared to prior art additives.

What is claimed is:

1. A compound which comprises an alkylphenyl poly(oxyalkylene) aminocarbamate having at least one basic nitrogen and an average molecular weight of about 800 to 6,000 and wherein the alkyl group of said alkylphenyl poly(oxyalkylene) aminocarbamate contains at least 40 carbon atoms and the poly(oxyalkylene) polymer is derived from $C_2$ to $C_5$ oxyalkylene units with the proviso that if the poly(oxyalkylene) polymer is a homopolymer of oxyethylene then the poly(oxyethylene) polymer does not contain more than 25 oxyethylene units.

2. A compound according to claim 1 wherein the alkyl group of said alkylphenyl poly(oxyalkylene) aminocarbamate contains from about 50 to about 200 carbon atoms.

3. A compound according to claim 2 wherein the alkyl group of said alkylphenyl poly(oxyalkylene) aminocarbamate contains from about 60 to 100 carbon atoms.

4. A compound according to claim 1 wherein the poly(oxyalkylene) polymer is derived from $C_3$ to $C_4$ oxyalkylene units.

5. A compound according to claim 1 wherein the poly(oxyalkylene) group of said alkylphenyl poly(oxyalkylene) aminocarbamate contains 1 to about 100 oxyalkylene units.

6. A compound according to claim 5 wherein the poly(oxyalkylene) group of said alkylphenyl poly(oxyalkylene) aminocarbamate contains 1 to about 25 oxyalkylene units.

7. A compound according to claim 6 wherein the oxyalkylene group of said alkylphenyl poly(oxyalkylene) aminocarbamate contains from 1 to about 10 oxyalkylene units.

8. A compound according to claim 1 wherein the aminocarbamate group of said alkylphenyl poly(oxyalkylene) aminocarbamate is derived from a polyamine having 2 to 12 amino nitrogen atoms and 2 to 40 carbon atoms.

9. A compound according to claim 8 wherein the polyamine is a polyalkylene polyamine having 2 to 12 amino nitrogen atoms and 2 to 24 carbon atoms.

10. A compound according to claim 9 wherein the polyalkylene polyamine is selected from the group consisting of ethylene diamine, propylene diamine, butylene diamine, pentylene diamine, hexylene diamine, diethylene triamine and dipropylene triamine.

11. A compound according to claim 10 wherein the polyalkylene polyamine is selected from the group consisting of ethylene diamine, propylene diamine, diethylen,e triamine and dipropylene triamine.

12. A compound according to claim 1 wherein said alkylphenyl poly(oxyalkylene) aminocarbamate has an average molecular weight of from about 1,000 to about 2,500.

13. A compound of Formula V $$R_m\text{-}C_6H_4\text{-}(OCH_2CH(R_1))_n\text{-}OC(O)\text{-}NH\text{-}(R_2NH)_p\text{-}H \quad V$$

wherein R is an alkyl group of at least 40 carbon atoms; $R_1$ is hydrogen or alkyl of from 1 to 3 carbon atoms; $R_2$ is alkylene of from 2 to 6 carbon atoms; m is an integer from 1 to 2; n is an integer such that the molecular weight of the compound is from about 800 to 6,000; and p is an integer from 1 to 6 and with the proviso that if $R_1$ is hydrogen then n is an integer from 1 to 25.

14. A compound according to claim 13 wherein R is an alkyl group of from about 50 to about 200 carbon atoms.

15. A compound according to claim 14 wherein R is an alkyl group of from about 60 to about 100 carbon atoms.

16. A compound according to claim 13 werein $R_1$ is methyl or ethyl.

17. A compound according to claim 13 wherein n is an integer from 1 to about 100.

18. A compound according to claim 17 wherein n is an integer from 1 to about 25.

19. A compound according to claim 18 wherein n is an integer from 1 to about 10.

20. A compound according to claim 13 wherein the compound of Formula V has an average molecular weight of from about 1,000 to 2,500.

* * * * *